United States Patent
Requieme et al.

(10) Patent No.: US 6,242,659 B1
(45) Date of Patent: *Jun. 5, 2001

(54) PROCESS FOR THE MANUFACTURE OF DIFLUOROMETHANE

(75) Inventors: Benoit Requieme, Charly; Sylvain Perdrieux, Vernaison; Bernard Cheminal, Saucieu-En-Jarrest; Eric Lacroix, Amberieux d' Azergues; Andre Lantz, Vernaison, all of (FR)

(73) Assignee: Elf Atochem, S.A., Puteaux (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/663,634

(22) Filed: Jun. 14, 1996

(30) Foreign Application Priority Data

Jun. 29, 1995 (FR) .................................................. 95 07821

(51) Int. Cl.$^7$ .................................................. C07C 17/08
(52) U.S. Cl. ..................... 570/169; 570/165; 570/166; 570/167; 570/168
(58) Field of Search ................................. 570/165, 166, 570/167, 168, 169

(56) References Cited

U.S. PATENT DOCUMENTS

| | | |
|---|---|---|
| H1129 | 1/1993 | Gumprecht . |
| 2,458,551 | 1/1949 | Benning . |
| 2,745,886 | 5/1956 | Ruh et al. . |
| 3,183,276 | 5/1965 | Vecchio et al. . |
| 3,446,622 | 5/1969 | Magagnoli et al. . |
| 3,632,834 | 1/1972 | Christoph, Jr. . |
| 3,644,545 | 2/1972 | Buckman . |
| 3,855,151 | 12/1974 | Schindel . |
| 3,880,661 | 4/1975 | Lau et al. . |
| 4,439,534 | 3/1984 | Foulletier . |
| 4,474,895 | 10/1984 | Foulletier . |
| 4,579,974 | 4/1986 | Cheminal et al. . |
| 4,579,976 | 4/1986 | Cheminal et al. . |
| 4,748,285 | 5/1988 | Foulletier . |
| 4,803,065 | 2/1989 | Itoh et al. . |
| 4,822,589 | 4/1989 | Kiyoura et al. . |
| 5,051,537 | 9/1991 | Manzer . |
| 5,136,113 | 8/1992 | Rao . |
| 5,227,350 | 7/1993 | Scott et al. . |
| 5,262,575 | 11/1993 | Dianis . |
| 5,407,877 | 4/1995 | Scott . |
| 5,494,876 | 2/1996 | Tsuji et al. . |
| 5,523,500 | 6/1996 | Cheminal et al. . |
| 5,672,786 | 9/1997 | Bonniface et al. . |
| 5,763,708 | 6/1998 | Clemmer et al. . |

FOREIGN PATENT DOCUMENTS

| | | |
|---|---|---|
| 44 19 534 C1 | 6/1994 | (DE) . |
| 821211 | 2/1957 | (EP) . |
| 0 055 958 | 12/1981 | (EP) . |
| 0 226 492 A1 | 11/1986 | (EP) . |
| 0 328 127 A1 | 2/1989 | (EP) . |
| 446 869 A1 | 3/1991 | (EP) . |
| 449 614 A2 | 3/1991 | (EP) . |
| 449 617 A2 | 3/1991 | (EP) . |
| 0 475 693 A1 | 9/1991 | (EP) . |
| 0 475 693 B1 | 9/1991 | (EP) . |
| 0 486 333 A1 | 10/1991 | (EP) . |
| 0 508 660 A1 | 3/1992 | (EP) . |
| 0 518 506 A2 | 5/1992 | (EP) . |
| 518 506 | 5/1992 | (EP) . |
| 508 660 | 10/1992 | (EP) . |
| 0 546 883 A1 | 11/1992 | (EP) . |
| 0 548 742 | 12/1992 | (EP) . |
| 0 554 165 A1 | 1/1993 | (EP) . |
| 0 690 832 B1 | 3/1994 | (EP) . |
| 0 657 408 A1 | 12/1994 | (EP) . |
| 0 657 409 A1 | 12/1994 | (EP) . |
| 0 685 262 A1 | 5/1995 | (EP) . |
| 0 751 108 A1 | 5/1996 | (EP) . |
| 0 805 136 A1 | 4/1997 | (EP) . |
| 0 821 211 A3 | 6/1997 | (EP) . |
| 2 501 062 | 12/1980 | (FR) . |
| 2501062 | 12/1980 | (FR) . |
| 55958 | 12/1980 | (FR) . |
| 486333 | 5/1992 | (FR) . |
| 546883 | 6/1993 | (FR) . |
| 657408 | 6/1995 | (FR) . |
| 657409 | 6/1995 | (FR) . |
| 49-134612 | 12/1974 | (JP) . |
| 51-82206 | 1/1975 | (JP) . |
| 51-082206 | 7/1976 | (JP) . |
| 56-038131 | 6/1979 | (JP) . |
| 60-1731 | 7/1985 | (JP) . |
| 62-023728 | 5/1986 | (JP) . |
| 1-262946 | 10/1989 | (JP) . |
| 5-32567 | 2/1991 | (JP) . |
| 4-321632 | 4/1991 | (JP) . |
| 5-50953 | 8/1991 | (JP) . |
| 43-10601 | 12/1992 | (JP) . |
| 6-263657 | 3/1993 | (JP) . |
| 6-263658 | 11/1993 | (JP) . |
| 5-339179 | 12/1993 | (JP) . |
| WO 93/25507 | 6/1993 | (WO) . |
| WO 94/21579 | 3/1994 | (WO) . |
| WO 94/21580 | 3/1994 | (WO) . |
| WO 95/12563 | 10/1994 | (WO) . |
| WO 97/11043 | 9/1996 | (WO) . |

*Primary Examiner*—Alan Siegel
(74) *Attorney, Agent, or Firm*—Smith, Gambrell & Russell, LLP

(57) ABSTRACT

The invention relates to the synthesis of difluoromethane by gas-phase catalytic fluorination of methylene chloride.

To lengthen the lifetime of the catalyst the operation is carried out in the presence of chlorine.

25 Claims, No Drawings

PROCESS FOR THE MANUFACTURE OF DIFLUOROMETHANE

FIELD OF THE INVENTION

The present invention relates to the field of fluorohydrocarbons and its subject is more particularly the manufacture of difluoromethane (F32) by catalytic fluorination of methylene chloride.

BACKGROUND OF THE INVENTION

Difluoromethane, known under the designation F32, is harmless to the ozone layer. It is therefore particularly advantageous for replacing CFCs. As a mixture with other hydrofluoroalkanes such as 1,1,1-trifluoroethane (F143a), 1,1,1,2-tetrafluoroethane (F134a) or pentafluoroethane (F125), it is intended especially to replace F22 (chlorodifluoromethane) and F502 (azeotropic mixture of F22 and of chloropentafluoroethane) in the field of refrigeration, of conditioned air and in other applications.

There are various known processes for the synthesis of F32. The hydrogenolysis of F12 (dichlorodifluoromethane) or of F22 (patents JP 60-01731 and EP 508 660) has the disadvantage of being generally not very selective and of producing worthless methane as by-product. It has recently been proposed to produce F32 by fluorination of bis (fluoromethyl) ether (patent EP 518 506).

It is also possible to produce F32 by fluorination of methylene chloride (F30) with anhydrous HF. Many patents describe this reaction, claiming the use of catalysts such as $Cr_2O_3$, $CrF_3$, $AlF_3$, Cr/carbon, $Ni/AlF_3$ etc.

The difficulty of this reaction lies in the stability of the catalyst, which tends either to coke rapidly or to crystallize. The problem becomes very tricky if it is intended to combine a high space time yield and a good selectivity while maintaining good stability of the catalyst.

To reduce this deactivation it has been proposed to employ specific catalysts such as a mechanical mixture of alumina and chromium oxide (patent GB 821 211). This patent gives an example for the fluorination of methylene chloride but the F32 space time yields obtained on this catalyst are low (<200 g/h/l) and the cumulative duration of the tests is shorter than 5 hours.

More generally, during fluorination reactions, it is very often envisaged to inject oxygen or air continuously in order to lengthen the lifetime of the catalysts. Thus, patent JP 51-82206 claims the use of 0.001 to 1% of oxygen to maintain the activity of catalysts prepared from chromium oxide. The examples in this patent relate only to reactions of fluorination of perhalogenated molecules ($CCl_4$, $C_2Cl_3F_3$).

The major disadvantage of this process is the appearance of a Deacon reaction. In fact, chromium oxide, well known as a fluorination catalyst, is also a good catalyst for the oxidation of HCl (patents U.S. Pat. No. 4,803,065 and U.S. Pat. No. 4,822,589). The oxygen introduced during the fluorination reaction reacts with the HCl formed to produce water and chlorine. Because of corrosion problems, the presence of water is particularly undesirable in a fluorination process.

Continuous introduction of a small quantity of chlorine has already been proposed in patent JP 49-134612, in order to stabilize the activity of the catalysts employed for the disproportionation of perhalogenated molecules; in this case the use of chlorine does not result in a decrease in the selectivity.

More recently the use of chlorine as an inhibitor of deactivation has also been described in the case of the fluorination of $CF_3CH_2Cl$ (US Statutory Invention Registration H1129). The examples which are presented clearly show that the use of chlorine makes it possible to maintain a stable space time yield of $CF_3CH_2F$ (F134a). On the other hand, no indication is given as to the effect of chlorine on the selectivity of the reaction.

However, in the case of hydrogenated molecules and in particular in the case of the fluorination of $CF_3CH_2Cl$ (F133a), the presence of chlorination reactions has been demonstrated, resulting in the formation of worthless by-products. Thus, in the case of the fluorination of F133a, by-products of the F120 series ($C_2HCl_nF_{5-n}$) are chiefly formed.

Given that the Deacon reaction produces chlorine, this loss in selectivity is also observed during the fluorination of hydrogenated molecules in the presence of oxygen on chromium catalysts. This is why some patents (see, for example, patent EP 546 883) have claimed the preparation of specific catalysts limiting the oxidation of HCl and the by-production of chlorine.

It could be assumed that the behaviour of methylene chloride would be similar to that of F133a, and this would make the use of chlorine not very advantageous for maintaining the activity of the catalyst. However, it has been surprising to find that, in the case of the methylene chloride fluorination, even with relatively high contents ($Cl_2/F30=3$ mol %), chlorine undergoes very little reaction with the compounds of the F30 series ($CH_2Cl_nF_{2-n}$), and this allows it to be employed without any significant decrease in the selectivity of the reaction.

In addition, in the abovementioned patent JP 51-82206 it is indicated that oxygen enables the catalyst activity to be maintained even in concentrations that are lower than that employed with chlorine. However, it has been found that, during the fluorination of methylene chloride, the continuous introduction of chlorine is, at an equal concentration, a more effective means than the addition of oxygen in order to stabilize the activity of the catalysts. In fact, in high space time yield conditions, oxygen addition is not sufficient to maintain the activity of the catalysts even at high temperature, whereas the addition of chlorine enables their lifetime to be significantly lengthened from a temperature of 250° C. upwards and therefore the fluorination of methylene chloride to be carried out in a temperature range in which an irreversible deactivation of the catalyst by crystallization is not very probable.

DESCRIPTION OF THE INVENTION

The subject of the present invention is therefore a process for the manufacture of difluoromethane by gas-phase catalytic fluorination of methylene chloride by means of anhydrous HF, characterized in that the operation is carried out in the presence of chlorine.

In accordance with the process according to the invention, chlorine (pure or diluted in an inert gas such as nitrogen or helium) is introduced into the reactor at the same time as methylene chloride and HF.

The $Cl_2/CH_2Cl_2$ molar ratio may vary within wide limits and is generally between 0.01% and 10%. A $Cl_2/CH_2Cl_2$ molar ratio of between 0.05 and 5% is preferably employed and, more particularly, a molar ratio of between 0.1% and 3%. It is also possible to introduce chlorine by dissolving it in methylene chloride.

The reaction temperature is generally between 200 and 450° C. However, the operation is preferably carried out at a temperature of between 250 and 380° C. in order to obtain a high space time yield without risking a deactivation of the catalyst due to crystallization.

The fluorination catalysts to be employed for making use of the process according to the invention may be bulk catalysts or supported catalysts, the support which is stable in the reaction mixture being, for example, an active carbon, an alumina, a partially fluorinated alumina, aluminium trifluoride or aluminium phosphate. Partially fluorinated alumina is intended to mean a composition which is rich in fluorine and contains chiefly aluminium, fluorine and oxygen in proportions such that the quantity of fluorine expressed as $AlF_3$ constitutes at least 50% of the total weight.

Among the bulk catalysts it is possible to mention more particularly chromium(III) oxide prepared according to any one of the methods known to a person skilled in the art (sol-gel process, precipitation of the hydroxide from chromium salts, reduction of chromic anhydride, and the like) and chromium trifluoride. Derivatives of metals such as nickel, iron, vanadium (in the oxidation state III), manganese, cobalt or zinc may also be suitable by themselves or in combination with chromium, in the form of bulk catalysts, as well as in the form of supported catalysts. Alkaline-earth metals, rare earths, graphite or alumina can also be incorporated in these catalysts or in their support in order to increase the thermal or mechanical stability thereof. During the preparation of catalysts using a number of metal derivatives in combination, the catalysts may be obtained by mechanical mixing or by any other technique, such as coprecipitation or a coimpregnation.

The supported or bulk catalysts can be employed in the form of beads, extrudates, tablets, or even, if operating in a stationary bed, in the form of fragments. When the operation is carried out in a fluid bed it is preferred to employ a catalyst in the form of beads or extrudates.

The supported or bulk catalysts are based on chromium and nickel. As nonlimiting examples of catalysts there may be mentioned:

chromium oxide microbeads obtained by the sol-gel process as described in patent FR 2 501 062, catalysts with chromium oxide deposited on active carbon (patent U.S. Pat. No. 4,474,895), on aluminium phosphate (patent EP 55 958) or on aluminium fluoride (U.S. Pat. Nos. 4,579,974 and 4,579,976), mixed chromium oxide and nickel chloride catalysts deposited on aluminium fluoride (patent application EP 0 486 333), bulk catalysts based on crystallized chromium oxide (patent application (EP 657 408), bulk catalysts based on nickel and chromium oxide (patent application EP 0 546 883), bulk catalysts based on vanadium and chromium oxide (patent application EP 0 657 409).

The abovementioned patents, the content of which is incorporated here by reference, describe broadly the method of preparation of these catalysts, as well as their method of activation, that is to say of preliminary conversion of the catalyst into stable active species by fluorination by means of gaseous HF diluted with compounds which are inert (nitrogen) or not (air or 1,1,2-trichloro-1,2,2-trifluoroethane). During this activation the metal oxides serving as active material (for example chromium oxide) or as support (for example alumina) may be partially or completely converted to corresponding fluorides.

Mixed catalysts based on chromium and nickel, which are described in patent applications EP 0 486 333 and EP 0 546 883 are more particularly preferred.

The contact time, defined as the ratio of the total flow rate of the reactants (measured in the reaction conditions) to the volume of catalyst, may vary within wide limits and is generally between 0.01 and 20 seconds. In practice it is preferable to work with contact times of between 0.1 and 5 seconds.

This reaction may be carried out at atmospheric pressure or at a higher pressure. A pressure of between 1 and 20 bar absolute is preferably chosen.

EXAMPLES

The following examples illustrate the invention without limiting it.

Example 1 a) Preparation and Activation of a Catalyst Based on Nickel and Chromium Which are Supported on Fluorinated Alumina 250 ml of partially fluorinated alumina (containing, in all, 83 mass % of aluminium fluoride and 16% of alumina) obtained beforehand by fluorination of alumina at about 300° C. with the aid of nitrogen and hydrofluoric acid are placed in a rotary evaporator. Before impregnation, this fluorinated support exhibits the following physicochemical characteristics:

| | |
|---|---|
| form: | beads 1–2 mm in diameter |
| apparent density: | 0.57 g/ml |
| BET surface: | 67 m$^2$/g |
| pore volume: | 0.72 ml/g (for pores with radius between 4 nm and 63 μm) |

An aqueous solution containing 12.5 g of chromic acid $CrO_3$ and 29 g of nickel chloride hexahydrate in 40 g of water, and a methanolic solution made up of 17.8 g of methanol in 50 g of water are added simultaneously onto the support, with stirring. The impregnation is performed over 45 minutes, at ambient temperature and at atmospheric pressure, on the support, with stirring.

After drying for 4 hours, under a stream of nitrogen, in a fluidized bed at about 110° C., the catalyst is next charged into a reactor made of Inconel 600 and activated as a stationary bed with a nitrogen/HF mixture according to the procedure described in patent EP 0 486 333. After this treatment the physicochemical characteristics of the Ni—Cr/$AlF_3$ catalyst activated in this way are the following:

| Chemical composition (by weight): | |
|---|---|
| fluorine: | 58.6% |
| aluminium: | 25.9% |
| nickel: | 6.4% |
| chromium: | 6.0% |

| Physical properties: | |
|---|---|
| volume of the pores with a radius of between 4 nm and 63 μm: | 0.4 ml/g |
| BET surface: | 23 m$^2$/g | b) Fluorination of Methylene Chloride 4 ml of this Ni—Cr/AlF$_3$ catalyst are charged into a tubular reactor made of Inconel 600, with an internal diameter of 1 cm and a volume of 40 ml and then, in a first stage, HF and chlorine are introduced at respective flow rates of 0.45 mol/h and 0.005 mol/h. Methylene chloride, vaporized in a preheater the temperature of which is set at 150° C., is next introduced in gaseous form into the reactor at a flow rate of 0.15 mol/h. The temperature of the reactor is maintained at 300° C. and the contact time in these conditions is 0.5 seconds.

On leaving the reactor, the reaction products are washed, dried and analysed by gas chromatography. The following table summarizes the results obtained after 48, 171, 338 and 527 hours' continuous operation.

| Duration (h) | Contact time (s) | HF/F30 molar ratio | F30 conversion (mol %) | Selectivity for F31 (mol %) | Selectivity for F32 (mol %) |
|---|---|---|---|---|---|
| 48 | 0.5 | 3.1 | 72.1 | 22.5 | 77.1 |
| 171 | 0.5 | 3.0 | 72.2 | 22.6 | 77.3 |
| 338 | 0.5 | 3.2 | 72.0 | 22.5 | 77.5 |
| 527 | 0.4 | 3.4 | 69.6 | 22.9 | 76.8 |

Despite a large addition of chlorine (3 mol %), the chlorination by-products remain in a minority in these reaction conditions. These by-products are chiefly F20 (trichloromethane), F21 (fluorodichloromethane), F22 (chlorodifluoromethane) and F23 (trifluoromethane).

In these reaction conditions the addition of chlorine allows a stable activity to be maintained with an F32 space time yield higher than 1100 g/h and a selectivity for F31+F32 higher than 99.5%.

Example 2 (Comparative)

The operation is carried out as in Example 1 on a fresh charge of the same Ni—Cr/AlF$_3$ catalyst, but with the chlorine feed stopped. The results, summarized in the following table, show that in the absence of chlorine the catalyst is deactivated very rapidly.

| Duration (h) | Contact time (s) | HF/F30 molar ratio | F30 conversion (mol %) | Selectivity for F31 (mol %) | Selectivity for F32 (mol %) |
|---|---|---|---|---|---|
| 22 | 0.5 | 3.2 | 48.9 | 31.0 | 69.0 |
| 49 | 0.5 | 3.2 | 38.8 | 36.3 | 63.7 |
| 75 | 0.5 | 3.0 | 24.9 | 57.6 | 42.3 |

Example 3 (Comparative)

The operation is carried out again as in Example 1 on a fresh charge of the same Ni—Cr/AlF$_3$ catalyst, but using oxygen introduced in the form of air instead of chlorine. The air flow rate is adjusted so that the O$_2$/CH$_2$Cl$_2$ molar ratio is 3%. The results are collated in the following table:

| Duration (h) | Contact time (s) | HF/F30 molar ratio | F30 conversion (mol %) | Selectivity for F31 (mol %) | Selectivity for F32 (mol %) |
|---|---|---|---|---|---|
| 24 | 0.5 | 3.1 | 64.2 | 24 | 76 |
| 90 | 0.5 | 3.0 | 46.6 | 35 | 65 |
| 188 | 0.5 | 3.1 | 35.5 | 46 | 54 |

It is concluded that oxygen does not enable the catalyst activity to be maintained. At the end of the fluorination test the solid is coked; its carbon weight content is 2.5%.

Example 4

The catalyst is a bulk chromium oxide which has a specific surface of 209 m$^2$/g and a pore volume (4 nm<r<63 μm) of 0.1 ml/g. This solid is employed after an activation with anhydrous HF. For this purpose the chromium oxide is first of all dried at 200° C. and then treated with an N$_2$/HF mixture at 200° C. When the initial exothermicity has subsided, the temperature is raised to 380° C. The catalyst is then maintained for 18 hours at 380° C. under a flow of pure anhydrous HF.

The activated catalyst has the following physicochemical properties:

| | |
|---|---|
| fluorine weight content: | 27% |
| chromium weight content: | 53% |
| Volume of the pores with a radius of between 4 nm and 63 μm: | 0.13 ml/g |
| BET surface: | 101 m$^2$/g. |

The fluorination of methylene chloride is carried out on this catalyst in the conditions of Example 1. After washing and drying, the analysis of the reaction products by gas chromatography gave the results which are brought together in the following table:

| Duration (h) | Contact time (s) | HF/F30 molar ratio | F30 conversion (mol %) | Selectivity for F31 (mol %) | Selectivity for F32 (mol %) |
|---|---|---|---|---|---|
| 52 | 0.3 | 3.0 | 66.4 | 24.4 | 73.3 |
| 72 | 0.3 | 2.9 | 66.8 | 24.4 | 75.0 |
| 96 | 0.3 | 2.9 | 67.2 | 23.8 | 73.8 |
| 117 | 0.3 | 2.8 | 66.5 | 24.3 | 73.9 |
| 212 | 0.3 | 2.9 | 65.9 | 24.3 | 73.7 |
| 300 | 0.3 | 3.0 | 68.2 | 23.0 | 73.9 |

As in Example 1 and in these reaction conditions, the chlorination products remain in a minority (selectivity for F31+F32>98%). The by-products are chiefly F20 (trichloromethane), F21 (fluorodichloromethane), F22 (chlorodifluoromethane) and F23 (trifluoromethane) and are formed with respective average selectivities of 0.5%, 0.1%, 0.1% and 1.3%.

Example 5

55 ml of the Ni—Cr/AlF$_3$ catalyst described in Example 1-a are charged into a tubular reactor made of Inconel 600, with an internal diameter of 21 mm and a volume of 150 ml, and then the reactants (HF, F30 and $Cl_2$) are fed at 300° C. and at a pressure of 1.5 MPa (absolute) at the following flow rates:

HF: 3 mol/hour

F30: 1 mol/hour $Cl_2$: 0.02 mol/hour

In these conditions the contact time on the catalyst is 15 seconds. On leaving the reactor the crude reaction gases are analysed by gas chromatography.

The following table summarizes the results obtained after 346 and 376 hours of continuous operation.

| Duration (h) | Contact time (s) | HF/F30 molar ratio | F30 conversion (mol %) | Selectivity for F31 (mol %) | Selectivity for F32 (mol %) |
|---|---|---|---|---|---|
| 346 | 15.0 | 3.1 | 66 | 25 | 72 |
| 376 | 15.1 | 3.0 | 65 | 25 | 72 |

The by-products of the F20 series remain in a minority. In these reaction conditions the continuous addition of chlorine allows a stable activity to be maintained with an F32 space time yield of 470 g/h per liter of catalyst and a selectivity for F31+F32 of 97%.

Example 6 (Comparative)

The operation of Example 5 is continued but with the chlorine feed cut off for 4 hours.

The results obtained after 383, 385 and 387 hours of continuous operation appear in the following table:

| Duration (h) | Contact time (s) | HF/F30 molar ratio | F30 conversion (mol %) | Selectivity for F31 (mol %) | Selectivity for F32 (mol %) |
|---|---|---|---|---|---|
| 383 | 14.9 | 2.8 | 67 | 27 | 69 |
| 385 | 14.9 | 2.8 | 63 | 29 | 68 |
| 387 | 14.9 | 2.8 | 60 | 30 | 67 |

It is found that the absence of chlorine, even for a few hours of operation, results in an appreciable drop in catalyst activity (approximately 13% in 4 hours), which causes a drop in the space time yield of F32 from 421 to 366 g/h per liter of catalyst.

Example 7

The operation is carried out under pressure (1.5 MPa absolute) as in Example 5, but on a fresh charge (35 ml) of the same Ni—Cr/$AlF_3$ catalyst and with a contact time of 5 seconds at 250° C. The reactant feed flow rates are the following:

HF: 6.6 mol/hour

F30: 2.2 mol/hour $Cl_2$: 0.04 mol/hour

The results obtained after 119, 500 and 785 hours of continuous operation in these conditions are collated in the following table:

| Duration (h) | Contact time (s) | HF/F30 molar ratio | F30 conversion (mol %) | Selectivity for F31 (mol %) | Selectivity for F32 (mol %) |
|---|---|---|---|---|---|
| 119 | 4.9 | 3.1 | 60.2 | 23.5 | 74.4 |
| 500 | 5.0 | 3.1 | 60.6 | 23.2 | 74.8 |
| 785 | 4.9 | 3.1 | 59.3 | 24.1 | 74.0 |

Despite a high space time yield of F32 (1435 g/h per liter of catalyst), the addition of chlorine makes it possible to maintain the activity of the catalyst and a selectivity for F31+F32 of approximately 98%.

What is claimed is:

1. Process for the manufacture of difluoromethane comprising gas-phase catalytic fluorination of methylene chloride with anhydrous hydrofluoric acid, carrying out the operation in the presence of chlorine and a fluorination catalyst, wherein formation of trichloromethane, fluorodichloromethane, chlorodifluoromethane, and trifluoromethane by-products are substantially avoided while stable catalyst is maintained.

2. Process according to claim 1, wherein the $Cl_2$/$CH_2Cl_2$ molar ratio is between 0.01% and 10%.

3. Process according to claim 1, wherein the operation is carried out at a temperature of between 200 and 450° C.

4. Process according to claim 1 wherein the catalyst is a bulk or supported catalyst based on (i) chromium or (ii) chromium and nickel.

5. Process according to one of claims 1, wherein the contact time is between 0.01 and 20 seconds.

6. Process according to claim 1, wherein the operation is carried out at a pressure of between 1 and 20 bar absolute.

7. Process according to claim 2, wherein the $Cl_2$/$CH_2Cl_2$ molar ratio is between 0.05% and 5%.

8. Process according to claim 2, wherein the $Cl_2$/$CH_2Cl_2$ molar ratio is between 0.1% and 3%.

9. Process according to claim 3, wherein the operation is carried out at a temperature of between 250 and 380° C.

10. Process according to claim 5, wherein the contact time is between 0.1 and 5 seconds.

11. Process for the manufacture of difluoromethane comprising gas-phase catalytic fluorination of methylene chloride with anhydrous hydrofluoric acid, carrying out the operation in the presence of chlorine and a fluorination catalyst based on chromium oxide and nickel, a $Cl_2$/$CH_2Cl_2$ molar ratio is between 0.1 and 3%, the operation is carried out at a temperature between 250 and 380° C., and contact time is between 0.1 and 5 seconds.

12. Process according to claim 1, wherein the catalyst is based on vanadium and chromium oxide.

13. Process according to claim 11 wherein the catalyst is chromium oxide and a nickel compound deposited on a support.

14. Process according to claim 11 wherein the catalyst is a bulk catalyst and is chromium oxide and a nickel compound.

15. Process according to claim 1 wherein the catalyst is a compound of a metal selected from the group consisting of chromium, nickel, iron, vanadium (III), manganese, cobalt and zinc.

16. Process according to claim 15 wherein the chromium is in the form of chromium oxide.

17. Process according to claim 15 wherein the catalyst is a bulk or supported catalyst.

18. Process according to claim 1 wherein the catalyst includes chromium in combination with a compound of a metal selected from the group consisting of nickel, iron, vanadium (III), manganese, cobalt and zinc.

19. Process according to claim 18 wherein the chromium is in the form of chromium oxide.

20. Process according to claim 18 wherein the catalyst is a bulk or supported catalyst.

21. Process for the manufacture of difluoromethane comprising gas-phase catalytic fluorination of methylene chloride with anhydrous hydrofluoric acid, carrying out the operation (1) in the presence of chlorine and a fluorination catalyst, and (2) at a temperature of at least 250° C. and in a temperature range in which deactivation of the catalyst due to crystallization is avoided, wherein formation of trichloromethane, fluorodichloromethane, chlorodifluoromethane, and trifluoromethane by-products are substantially avoided while stable catalyst is maintained.

22. Process according to claim 21 wherein the operation is carried out at a temperature between 250 and 450° C.

23. Process according to claim 1 wherein the catalyst is a bulk or supported mixed catalyst based on chromium and nickel.

24. Process according to claim 21 wherein the $Cl_2/Ch_2Cl_2$ molar ratio is between 0.1 and 3%, the temperature is between 250 and 380° C., the contact time is between 0.1 and 5 seconds, and the pressure is between 1 and 20 bar absolute.

25. Process according to claim 21 wherein the methylene chloride is vaporized in a preheater and thereafter introduced in a gaseous state into a reactor where the gas-phase catalytic fluorination reaction occurs.

* * * * *